United States Patent

Phillips et al.

Patent Number: 6,072,057

Date of Patent: *Jun. 6, 2000

[54] 1H-4(5)-CYCLO-SUBSTITUTED IMIDAZOLE DERIVATIVES AS HISTAMINE $H_3$ RECEPTOR AGENTS

[75] Inventors: James G. Phillips, Bay Village; Amin Mohammed Khan, Solon; Clark E. Tedford, South Russel, all of Ohio

[73] Assignee: Gliatech Inc., Cleveland, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/973,121

[22] PCT Filed: Jun. 6, 1996

[86] PCT No.: PCT/US96/09498

§ 371 Date: Feb. 11, 1998

§ 102(e) Date: Feb. 11, 1998

[87] PCT Pub. No.: WO96/40126

PCT Pub. Date: Dec. 19, 1996

[51] Int. Cl.[7] ........................ A61K 31/4164; A61K 31/42; C07D 233/61; C07D 261/02
[52] U.S. Cl. ..................... 548/240; 514/378; 514/400; 548/335.5
[58] Field of Search ................ 548/240, 335.5; 514/378, 400

[56] References Cited

U.S. PATENT DOCUMENTS

| | | | |
|---|---|---|---|
| 3,711,495 | 1/1973 | Kulsa et al. | 548/240 X |
| 4,080,340 | 3/1978 | Kulsa et al. | 548/240 X |
| 4,767,778 | 8/1988 | Arrang et al. | 514/397 |
| 4,987,146 | 1/1991 | Rohoe et al. | 514/397 |
| 5,156,669 | 10/1992 | Zierke et al. | 548/240 X |

FOREIGN PATENT DOCUMENTS

| | | |
|---|---|---|
| WO 93/12093 | 6/1993 | WIPO . |
| WO 93/12107 | 6/1993 | WIPO . |
| WO 93/12108 | 6/1993 | WIPO . |

OTHER PUBLICATIONS (Schwartz, 1975) *Life Sci.* 1.7: 503–518.
(Inagaki et al., 1988)*J. Comp. Neurol.* 273: 282–300.
(Schwartz et al., 1986) *TIPS* 8: 24–28.
(Arrang et al., 1983) *Nature* 302: 832–837.
(Lin et al., 1990) *Brain Res.* 529: 325–330.
S.M. Berge et a., "Pharmaceutical Salts," *J. Pharm. Sci.*, 6.6: 1–19 (1977).
West et al., (1990) *Mol. Pharmacol.* 3.8 610–613.
Poste et al., "Lipid Vesicles as Carriers for Introducing Biologically Active Materials Into Cells," Chapter 4: 33–71.
Archiv der Parmazie (D 1358 E) *Archiv der Pharmazie*, (1973) Band 306: 933–940.

*Primary Examiner*—Floyd D. Higel
*Attorney, Agent, or Firm*—Rockey, Milnamow & Katz; Martin L. Katz, Esq.

[57] ABSTRACT

The present invention is directed to 1H-4(5)-substituted imidazole derivates of formula (I),

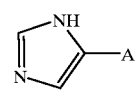

(I)

wherein A is (a); (b); or (c)

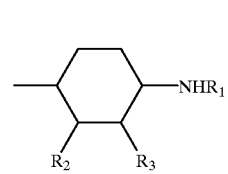

(a)

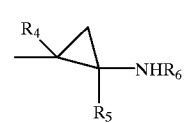

(b)

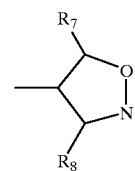

(c)

wherein $R_1$ is lower alkyl or lower alkoxy;

$R_2$, $R_3$, $R_4$, $R_5$, $R_7$ and $R_8$ are each independently hydrogen or lower alkyl;

$R_6$ is hydrogen, lower alkyl or lower alkoxy and $R_5$ and $R_6$ can be joined to form a 4, 5 or 6 membered ring.

The compounds of formula (I) have $H_3$ histamine receptor agonist activity. The pharmaceutically acceptable salts, and individual stereoisomers of compounds of formula (I) above, as well as mixtures thereof, are also contemplated as falling within the scope of the present invention. The present invention also provides pharmaceutical compositions comprising a pharmaceutically acceptable carrier in combination with an effective amount of a compound of formula (1). The present invention also provides a method of treating conditions in which activation of histamine $H_3$ receptors may be of therapeutic importance such as allergy, inflammation, cardio or cerebrovascular disease, gastrointestinal disorders and CNS disorders involving psychiatric disorders.

17 Claims, No Drawings

1H-4(5)-CYCLO-SUBSTITUTED IMIDAZOLE DERIVATIVES AS HISTAMINE H$_3$ RECEPTOR AGENTS

This Application is an application filed under Sec. 371 of PCT/US96/09498 filed Jun. 6, 1996.

TECHNICAL FIELD

This invention relates to compounds having pharmacological activity, to compositions containing these compounds, and to a medical method of treatment employing the compounds and compositions. More particularly, this invention concerns 1H-4(5)-substituted imidazole derivatives and their salts or solvates. These compounds have H$_3$ histamine receptor agonist activity. This invention also relates to pharmaceutical compositions containing these compounds, and to a method of treating disorders in which histamine H$_3$ receptor activation is beneficial.

BACKGROUND OF THE INVENTION

Histamine is a chemical messenger involved in various complex biological actions. When released histamine interacts with specific macromolecular receptors on the cell surface or within a target cell to elicit changes in many different bodily functions. Various cell types including smooth muscle, blood cells, cells of the immune system, endocrine and exocrine cells as well as neurons respond to histamine by stimulating the formation of intracellular signals, including formation of phosphatidylinositol or adenylate cyclase. Evidence that histamine plays a role as a neurotransmitter was established by the mid to late 1970's (Schwartz, 1975) *Life Sci.* 17: 503–518. Immunohistochemical studies identified histaminergic cell bodies in the tuberomammillary nucleus of the posterior hypothalamus with widespread projections in the dicencephalon and telencephalon (Inagaki et al., 1988) *J. Comp. Neurol.* 273: 283–300.

Identification of two histamine receptors (H$_1$ and H$_2$) was reported to mediate the biochemical actions of histamine on neurons. Recently, studies have demonstrated the existence of a third subtype of histamine receptor, the histamine H$_3$ receptor (Schwartz et al., 1986) *TIPS* 8: 24–28. Various studies have now demonstrated that histamine H$_3$ receptors are found on the histaminergic nerve terminals in the brains of several species, including man (Arrang et al., 1983) *Nature* 302: 832–837. The H$_3$ receptor found on the histaminergic nerve terminal was defined as an autoreceptor and could intimately control the amount of histamine released from the neurons. Histamine, the natural compound, was capable of stimulating this autoreceptor but when tested against known H$_1$ and H$_2$ receptor agonists and antagonists, a distinct pharmacological profile emerged. Further, H$_3$ receptors have been identified on cholinergic, serotoninergic and monoamine nerve terminals in the peripheral nervous system (PNS) and central nervous system including the cerebral cortex and cerebral vessels. These observations suggest that H$_3$ receptors are uniquely located to modulate histamine as well as other neurotransmitter release, and H$_3$ agonists could be important mediators of neuronal activity.

As stated, CNS histaminergic cell bodies are found in the magnocellular nuclei of the hypothalamic mammillary region and these neurons project diffusely to large areas of the forebrain. The presence of histaminergic cell bodies in the tuberomamillary nucleus of the posterior hypothalamus, a brain area involved in the maintenance of wakefulness, and their projections to the cerebral cortex suggest a role in modulating the arousal state or sleep-wake cycle. The histaminergic projection to many limbic structures such as the hippocampal formation and the amygdaloid complex suggest roles in functions such as autonomic regulation, control of emotions and motivated behaviors, and memory processes.

The concept that histamine is important for the state of arousal, as suggested by the location of histaminergic pathways, is supported by other types of evidence. Lesions of the posterior hypothalamus is well known to produce sleep. Neurochemical and electrophysiological studies have also indicated that the activity of histaminergic neurons is maximal during periods of wakefulness and is suppressed by barbiturates and other hypnotics. Intraventricular histamine induces the appearances of an arousal EEG pattern in rabbits and increased spontaneous locomotor activity, grooming and exploratory behavior in both saline ad pentobarbital-treated rats.

In contrast, a highly selective inhibitor of histidine decarboxylase, the sole enzyme responsible for histamine synthesis, has been shown to impair waking in rats. These data support the hypothesis that histamine may function in modulating behavioral arousal. The role of the H$_3$ receptor in sleep-waking parameters has been recently demonstrated (Lin et al., 1990) *Brain Res.* 529: 325–330. Oral administration of RAMHA, a H$_3$ agonist, caused a significant increase in deep slow wave sleep in the cat. Conversely, thioperamide, a H$_3$ antagonist, enhanced wakefulness in a dose-dependent fashion. Thioperamide has also been shown to increase wakefulness and decrease slow wave and REM sleep in rats. These findings are consistent with in vivo studies demonstrating that RAMHA, can decrease and conversely, thioperamide can increase the synthesis and release of histamine. Together, these data suggest that selective H$_3$ agonists may be useful in the treatment of hyperarousal states such as sleep disorders characterized by hyposomnolence or insomnia.

Serotonin, norepinephrine, dopamine, and acetylcholine release have all been demonstrated to be to regulated by the histamine H$_3$ receptor. These neurotransmitters are known to play a role in many CNS psychiatric disorders involving emotional or higher cognitive function. Consequently, an H$_3$ receptor agonist would therefore be expected to decrease the release of these neurotransmitters in brain. H$_3$ receptor agonists might reduce states of hyperarousal via decreasing levels of neurotransmitter release and provide therapeutic approaches to the treatment of various CNS diseases characterized by emotional imbalance, anxiety or hyperarousal.

H$_3$ receptor agonists may be useful in treating several other CNS disorders. It has been suggested that histamine may be involved in the control of sleep/wake states, states of arousal and alertness, cerebral circulation and migraine, energy metabolism, and hypothalmic hormone secretion.

In spite of their low density, H$_3$ receptor binding sites can be detected outside the brain. The presence of H$_3$ receptors on the sympathetic and parasympathetic nerve terminals suggest uses of H$_3$ agonists in regulating the peripheral autonomic nervous system. Several studies have revealed the presence of H$_3$ heteroreceptors in the gastrointestinal tract, as well as upon neurons of the respiratory tract. Accordingly, an H$_3$ receptor agonist may be useful in the treatment of diseases and conditions such as allergy, asthma, rhinitis, airway congestion, inflammation, hyper and hypo motility and acid secretion of the gastrointestinal tract. Peripheral or central stimulation of H$_3$ receptors may also contribute to changes in blood pressure, heart rate and cardiovascular output and could be used in the treatment of cardiovascular diseases. Recent evidence has indicated the possible use of $H_3$ agonists in the treatment of cardiac ischemia and glaucoma.

U.S. Pat. No. 4,767,778 (Aug. 30, 1988) discloses compounds of the general formula:

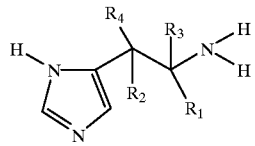

in which $R_1$, $R_2$, $R_3$, and $R_4$ are each hydrogen, or methyl, and at least one but not more than two of $R_1$, $R_2$, $R_3$, and $R_4$ are methyl, or two of $R_1$, $R_2$, $R_3$, and $R_4$ are together methylene.

WO 93/12107 (Jun. 24, 1993) discloses compounds of general formula:

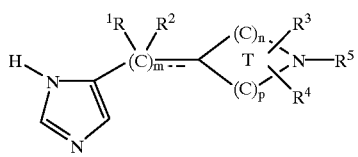

where m is an integer selected from the group consisting of 1 and 2;

n and p are integers and are each independently selected from the group consisting of: 0, 1, 2, 3, and 4 such that the sum of n and p is 4 and T is a 6-membered ring;

$R^3$ and $R^4$ are each independently bound to the same or different carbon atom of ring T such that there is only one $R^3$ group and one $R^4$ group in ring T, and each $R^1$, $R^2$, $R^3$, and $R^4$ is independently selected from the group consisting of:

(1) H;

(2) $C_1$ to $C_6$ alkyl; and (3) —$(CH_2)_q$—$R^6$ wherein q is an integer of: 1 to 7, and $R^6$ is selected from the group consisting of: phenyl, substituted phenyl, —$OR^7$, —$C(O)OR^7$, —$C(O)R^7$, —$OC(O)R^7$, —$C(O)NR^7R^8$, CN and —$SR^7$ wherein the substituents on said substituted phenyl are each independently selected from the group consisting of: —OH, —O—($C_1$ to $C_6$) alkyl, halogen, $C_1$ to $C_6$ alkyl, —$CF_3$, —CN, and —$NO_2$, and wherein said substituted phenyl contains from 1 to 3 substituents; $R^5$ is selected from the group consisting of:

(1) H;

(2) $C_1$ to $C_{20}$ alkyl;

(3) $C_3$ to $C_6$ cycloalkyl;

(4) —$C(O)OR^{7'}$; wherein $R^{7'}$ is the same as $R^7$ defined below except that $R^{7'}$ is not H;

(5) —$C(O)R^7$;

(6) —$C(O)NR^7R^8$;

(7) allyl;

(8) propargyl; and (9) —$(CH_2)_q$—$R^6$, wherein q and $R^6$ are defined as above, and when q is equal to 1, then $R^6$ is not OH or SH; $R^7$ and $R^8$ are each independently selected from the group consisting of: H, $C_1$ to $C_6$ alkyl, and $C_3$ to $C_6$ cycloalkyl; the dotted line (-----) represents a double bond that is optionally present when m is 1, and n is not 0, and p is not 0 (i.e., the nitrogen in the ring is not bound directly to the carbon atom bearing the double bond), and when said double bond is present then $R^2$ is absent; and when m is 2, each $R^1$ is the same or different substituent for each m, and each $R^2$ is the same or different for each m, and at least two of the sustituents $R^1$ and/or $R^2$ are H.

WO 93/12108 (Jun. 24, 1993) discloses compounds of general formula:

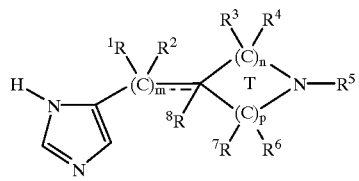

where m is an integer selected from the group consisting of 0, 1, and 2;

n and p are integers and are each independently selected from the group consisting of: 0, 1, 2, 3, and 4 such that the sum of n and p is 2 or 3 such that the sum of n and p is 2, T is a 4-membered ring and when the sum of n and p is 3, T is a 5-membered ring;

each $R^1$, $R^2$, $R^3$, $R^4$, $R^6$, $R^7$, and $R^8$ is independently selected from the group consisting of:

(1) H;

(2) $C_1$ to $C_6$ alkyl;

(3) $C_3$ to $C_6$ cycloalkyl; and (3) —$(CH_2)_q$—$R^9$ wherein q is an integer of: 1 to 7, and $R^9$ is selected from the group consisting of: phenyl, substituted phenyl, —$OR^{10}$, —$C(O)OR^{10}$, —$C(O)R^{10}$, —$OC(O)R^{10}$, —$C(O)NR^{10}R^{11}$, CN and —$SR^{10}$ wherein $R^{10}$ and $R^{11}$ are defined below, and wherein the substituents on said substituted phenyl are each independently selected from the group consisting of: —OH, —O—($C_1$ to $C_6$) alkyl, halogen, $C_1$ to $C_6$ alkyl, —$CF_3$, —CN, and —$NO_2$, and wherein said substituted phenyl contains from 1 to 3 substituents; examples of —$(CH_2)_q$—$R^9$ include benzyl, substituted benzyl and the like, wherein the substituents on the substituted benzyl are as defined above for said substituted phenyl; $R^5$ is selected from the group consisting of:

(1) H;

(2) $C_1$ to $C_{20}$ alkyl;

(3) $C_3$ to $C_6$ cycloalkyl;

(4) —$C(O)OR^{10'}$; wherein $R^{10'}$ is the same as $R^{10}$ defined below except that $R^{10'}$ is not H;

(5) —$C(O)R^{10}$;

(6) —$C(O)NR^{10}R^{11}$;

(7) allyl;

(8) propargyl; and (9) —$(CH_2)_q$—$R^9$, wherein q and $R^9$ are defined as above, and when q is equal to 1, then $R^9$ is not —OH or —SH; $R^{10}$ and $R^{11}$ are each independently selected from the group consisting of: H, $C_1$ to $C_6$ alkyl, and $C_3$ to $C_6$ cycloalkyl; and for the substituent —$C(O)NR^{10}R^{11}$, $R^{10}$ and $R^{11}$, together with them nitrogen to which they are bound, can form a ring having 5,6, or 7 atoms; the dotted line (---) represents a double bond that is optionally present when m is 1, and T is a 5-membered ring, and n is not 0, and p is not 0

(i.e., the nitrogen in the ring is not bound directly to the carbon atom bearing the double bond), and when said double bond is present then $R^2$ and $R^8$ are absent; when m is 2, each $R^1$ is the same or different substituent for each m, and each $R^2$ is the same or different for each m; when n is 2 or 3, each $R^3$ is the same or different substituent for each n, and each $R^4$ is the same or different substituent for each n; and when p is 2 or 3, each $R^6$ is the same or different substituent for each p, and each $R^7$ is the same or different substituent for each p.

WO 93/12093 (Jun. 24, 1993) discloses compounds of general formula:

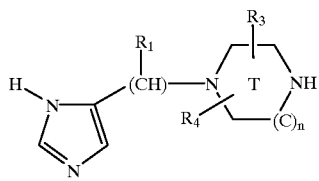

where n is 1 or 2, such that when n is 1 then ring T is a six membered ring, and when n is 2 then ring T is a seven membered ring;

$R^1$ is selected from the group consisting of:
(1) H;
(2) $C_1$ to $C_6$ alkyl;
(3) allyl; and
(4) propargyl;

$R^3$ and $R^4$ are independently selected from the group consisting of:
(1) H;
(2) $C_1$ to $C_6$ alkyl;
(3) allyl; and
(4) propargyl;
(5) —$(CH_2)_q$—$R^5$ wherein q is an integer of: 1 to 7, and $R^5$ is selected from the group consisting of: phenyl, substituted phenyl, —$OR^6$, —$C(O)OR^6$, —$C(O)R^6$, —$OC(O)R^6$, —$C(O)NR^6R^7$, CN and —$SR^6$ wherein $R^6$ and $R^7$ are as defined below, and wherein the substituents on said substituted phenyl are each independently selected from the group consisting of: —OH, —O—($C_1$ to $C_6$) alkyl, halogen, $C_1$ to $C_6$ alkyl, —$CF_3$, —CN, and —$NO_2$, and wherein said substituted phenyl contains from 1 to 3 substituents; $R^6$ and $R^7$ are each independently selected from the group consisting of: H and $C_1$ to $C_6$ alkyl; and $R^3$ and $R^4$ are each independently bound to the same or different carbon atom of ring T.

4(5)-(4-Aminocyclohexyl)-1H-imidazole is disclosed in Arch. Pharmaz. p.934–942, vol. 306, 1973 by W. Schunack and was shown to be inactive as an antihistamine agent.

2-(4-imidazoyl)-cyclopropylamine when tested as a racemic mixture is disclosed as having moderate $H_3$ histamine receptor agonist activity in U.S. Pat. No. 4,767,778.

SUMMARY OF THE INVENTION

The present invention is directed to 1H-4(5)-substituted imidazole derivatives of formula I:

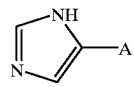

wherein A is

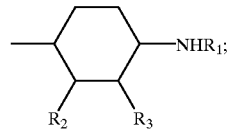

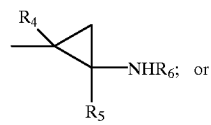

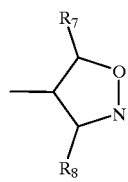

where $R_1$ is lower alkyl or lower alkoxy;

$R_2, R_3, R_4, R_5, R_7$ and $R_8$ are each independently hydrogen or lower alkyl;

$R_6$ is lower alkyl or lower alkoxy and $R_5$ and $R_6$ can be joined to form a 4, 5, or 6 membered ring.

The compounds of formula I have $H_3$ histamine receptor agonist activity.

The pharmaceutically acceptable salts, prodrugs and individual stereoisomers of compounds of formula I above, as well as mixtures thereof, are also contemplated as falling within the scope of the present invention.

The present invention also provides pharmaceutical compositions comprising a pharmaceutically acceptable carrier in combination with an effective amount of a compound of formula I.

The present invention also provides a method of treating conditions in which activation of histamine $H_3$ receptors may be of therapeutic importance such as allergy, inflammation, cardio or cerebrovascular disease (i.e. hyper or hypotension, ischemia, stroke, migraine), gastrointestinal disorders (acid secretion, motility) and CNS disorders involving psychiatric disorders (i.e., including anxiety, manic/depressive disorder, schizophrenia, obsessive-compulsive disorders, etc.) and sleep disorders (i.e., sleep apnea, insomnia, biological and circadian rhythms, hyper and hyposomnolence and related disorders) hypothalamic dysfunction (i.e., eating disorders such as anorexia/bulimia, thermoregulation, hormone release) comprising administering an effective amount to a patient in need of such treatment of a compound of formula I:

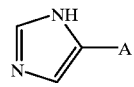

I wherein A is

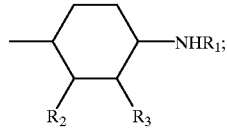

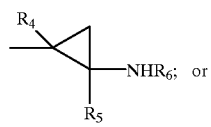

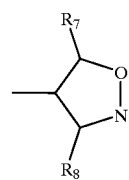

where

R₁ is hydrogen, lower alkyl or lower alkoxy;

R₂, R₃, R₄, R₅, R₇ and R₈ are each independently hydrogen or lower alkyl;

R₆ is hydrogen, lower alkyl or lower alkoxy and R₅ and R₆ can be joined to form a 4, 5 or 6 membered ring.

When R₅ and R₆ are joined together to form a 4, 5 or 6 membered ring, groups such as pyrrolidine, piperidine, oxaazacyclopentane, oxaazacyclobutane and oxaazacyclohexane groups are formed.

DETAILED DESCRIPTION OF THE INVENTION

Representative novel compounds of this invention include compounds of the formula:

(1.0)

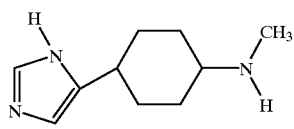

(2.0)

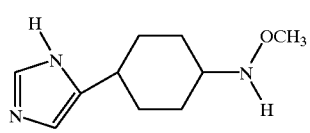

-continued (3.0)

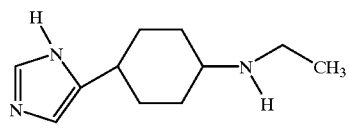

(4.0)

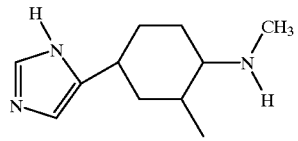

(5.0)

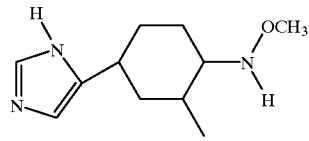

(6.0)

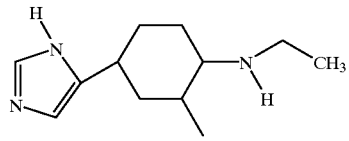

(7.0)

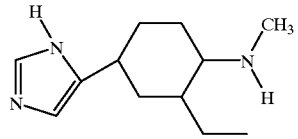

(8.0)

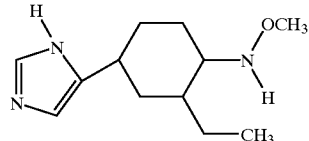

(9.0)

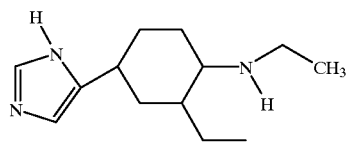

(10.0)

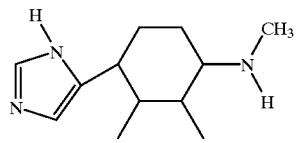

(11.0)

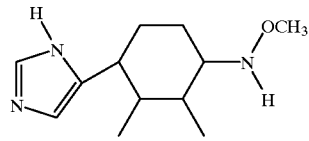

(12.0)

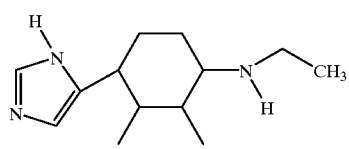

-continued
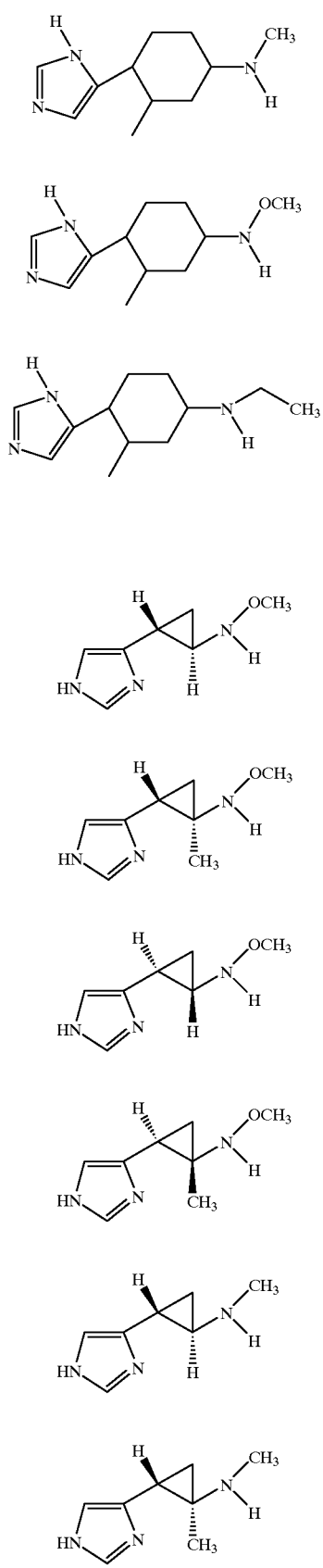
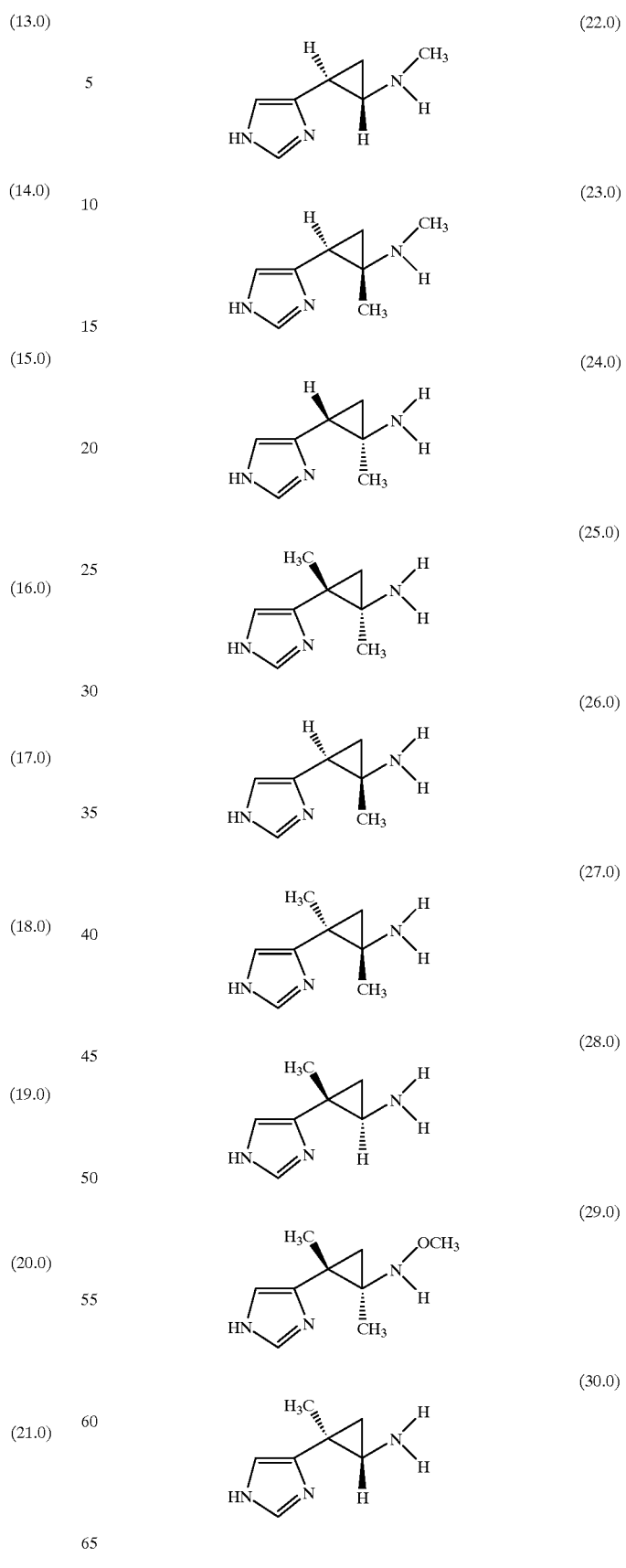

(31.0) 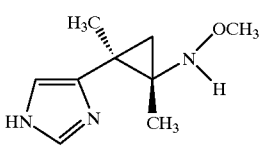

(32.0) 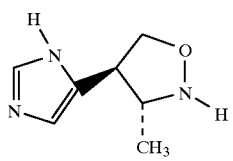

(33.0) 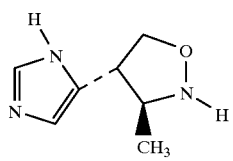

(34.0) 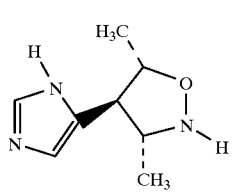

(35.0) 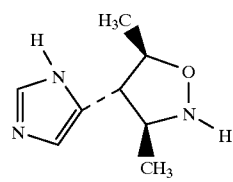

(36.0) 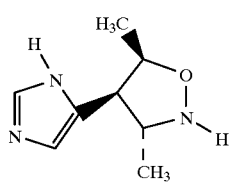

(37.0) 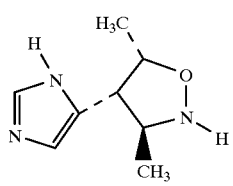

(38.0) 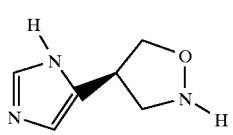

(39.0) 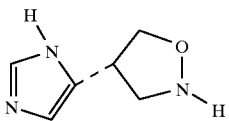

Certain compounds of the invention may exist in different isomeric (e.g., enantiomers and diastereoisomers) forms. The invention contemplates all such isomers both in pure form and in admixture, including racemic mixtures. Enol forms are also included.

The compounds of formula (1.0) can exist in unhydrated as well as hydrated forms, e.g., hemi-hydrate, mono-, tetra-, decahydrates, etc. The water may be removed by heating or other means to form the anhydrous compound. In general, the hydrated forms, with pharmaceutically acceptable solvents such as water, ethanol, and the like are equivalent to the unhydrated forms for the purposes of the invention.

Certain compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, fumaric, succinic, ascorbic, maleic, methanesulfonic and othermineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide, potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," *J. Pharm. Sci.*, 66: 1–19 (1977) which is incorporated herein by reference.

As throughout this specification and appended claims, the following terms have the meanings ascribed to them:

Prodrugs of the compounds of the present invention are also contemplated and are included within the scope of the present invention.

As used herein, the term "prodrug" shall mean a derivative of a compound which undergoes in vivo hydrolysis to the parent compound or an analog which is metabolically transformed to a biologically active compound.

Prodrugs are often employed to improve pharmaceutical or biological properties, as for example solubility, melting point, stability and related physicochemical properties properties, absorption, pharmacodynamics and other delivery related properties.

The term "alkyl" as used herein refers to straight or branched chain radicals derived from saturated hydrocarbons by the removal of one hydrogen atom. Representative examples of alkyl groups include methyl, ethyl, n-propyl, iso-propyl, n-butyl, sec-butyl, iso-butyl, tert-butyl, and the like.

The term "alkoxy" as used herein refers to the radical —O-alkyl where alkyl is as defined herein. Representative examples of alkoxy groups as used herein include methoxy, ethoxy, n-propxy, iso-propxy, n-butoxy, tert-butoxy, and the like.

Individual enantiomeric forms of compounds of the present invention can be separated from mixtures thereof by techniques well known in the art. For example, a mixture of diastereoisomeric salts may be formed by reacting the compounds of the present invention with an optically pure form of the acid, followed by purification of the mixture of diastereoisomers by recrystallization or chromatography and subsequent recovery of the resolved compound from the salt by basification. Alternatively, the optical isomers of the compounds of the present invention can be separated from one another by chromatographic techniques employing separation on an optically active chromatographic medium.

The present invention also provides pharmaceutical compositions which comprise one or more of the compounds of formula 1 above formulated together with one or more nontoxic pharmaceutically acceptable carriers. The pharmaceutical compositions may be specifically formulated for oral administration in solid or liquid form, parental injection, or for rectal administration.

The pharmaceutical compositions of this invention can be administered to humans and other animals orally, rectally, parenterally, intracisternally, intravaginally, intraperitoneally, topically as by being within the scope of this invention. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as perservative, wetting agents, emulsifying in some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylccilulose, alginates, gelatin, polyvinylpyrrolidine, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hardfilled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredients(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum methydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology,* Volume XIV, Academic Press, New York, N.Y. (1976) p.33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also comtemplated as being within the scope of the invention.

The following processes and techniques may be employed to produce compounds of formula the present invention. The reactions are performed in a solvent appropriate to the reagents and materials employed and suitable for the transformation being effected. It is understood by those skilled in the art of organic synthesis that the functionality present in the molecule must be consistent with the chemical transformation proposed. This will frequently necessitate judgement as to the order of synthetic steps, protecting groups required and deprotection conditions.

A. Preparation of Cyclohexyl Derivatives

Cyclohexyl derivatives of formula I cannot be prepared in the same manner as 4(5)-(4-aminocyclohexyl)-1H-imidazole as disclosed (Schunack et. al., 1973) *Arch. Pharmaz.* 306: 934–942. These compounds are prepared according to scheme I.

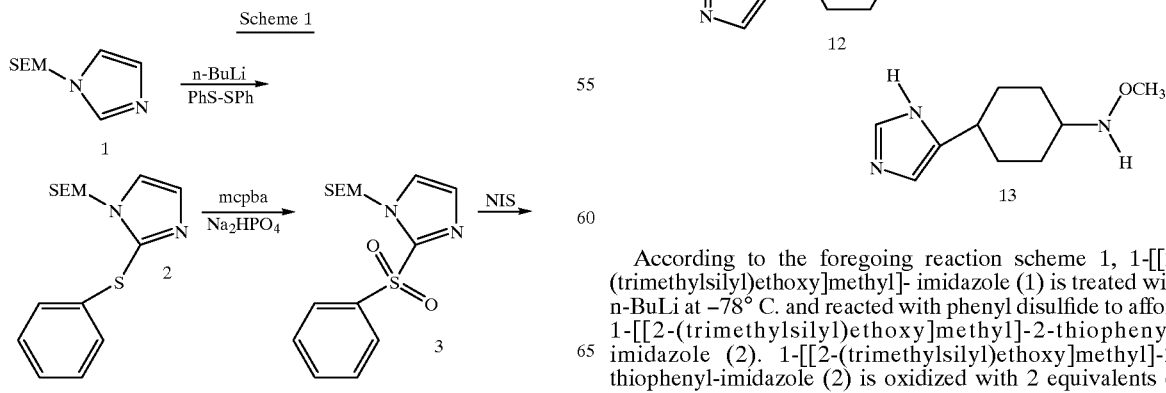

According to the foregoing reaction scheme 1, 1-[[2-(trimethylsilyl)ethoxy]methyl]- imidazole (1) is treated with n-BuLi at −78° C. and reacted with phenyl disulfide to afford 1-[[2-(trimethylsilyl)ethoxy]methyl]-2-thiophenyl-imidazole (2). 1-[[2-(trimethylsilyl)ethoxy]methyl]-2-thiophenyl-imidazole (2) is oxidized with 2 equivalents of m-chloroperbenzoic acid to give 1-[[2-(trimethylsilyl)

ethoxy]methyl]-2-sulfonylphenyl-imidazole (3). 1-[[2-(trimethylsilyl)ethoxy]methyl]-2-sulfonylphenyl-imidazole (3). is deprotonated with lithium diisopropylamide at −78°C. and treated with N-iodosuccinimide to afford 1-[[2-(trimethylsilyl)ethoxy]methyl]-2-sulfonylphenyl-5-iodo-imidazole (4). The corresponding grignard reagent of (4) is prepared by treatment with 1 equivalent of t-butyl magnesium chloride at 0° C. in anhydrous $CH_2Cl_2$ for 30 minutes and then reacted with 1,4-cyclohexanedione mono-ethylene ketal (5) to provide alcohol (6). The sulfonylphenyl protecting group is removed by treatment of (6) in methanol at 0° C. in the presence of 4 equivalents of sodium phosphate buffer with excess 2–3% Na(Hg) to give alcohol (7). Alcohol (7) is dehydrated by heating in THF/2 drops of water in the presence of a catalytic amount of PPTS to give olefin (8). The SEM protecting group is removed by treatment of (8) with n-butyl ammonium flouride at 60° C. to provide olefin (9). Catalytic hydrogenation of (9) over Pd(C) affords cyclohexane (10). Ketal deprotection of (10) proceeds smoothly with 5% HCl in THF at room temperature to give (1H-4(5)-imidazoyl)-4-cyclohexanone (11). The N-methoxy oxime is prepared by treatment of ketone (11) with N-methoxyl amine and TEA in dichloromethane to give (12). Finally, TBAH reduction of oxime (12) affords the (1H-(4,5)-imidazoyl)-4-cyclohexyl-N-methoxylamine (13).

Scheme II

Chiral cyclopropane containing compounds that are claimed as histamine $H_3$ receptor receptor agonists were prepared from 3-[(1-triphenylmethyl-4-imidazoyl)]-2(R)-3(R)-cyclopropanoic butyl ester (14) or 3-[(1-triphenylmethyl-4-imidazoyl)]-2(1S,2S)-cyclopropanoic butyl ester (15). The racemic mixture of these enantiomers was separated using a chiral column (Regis serial #0112201) and a mobile phase of 90/10 Hexane/Isopropyl alcohol. Using this column, enantiomer (15) had a retention time of 7.315 minutes, and enantiomer (14) had a retention time of 5.787 minutes.

The enatiomerically pure ester (14) is saponified with KOH to give acid (16). Treatment of acid (16) with ethyl chloroformate in the presence of TEA provides a mixed anhydride which is reacted in situ with sodium azide to give the acyl azide (17). Heating the acyl azide (17) in ethanol at 80° C. affords the ethyl carbamate (18) which is hydrolyzed to the corresponding 2(R)-(1-triphenylmethyl-4-imidazoyl)-3(R)-cyclopropylamine (19). Deprotection of the trityl group with HCl provides 2-(R)(1H)-4-imidazoyl)-3(R)-cyclopropylamine-cyclopropylamine (20).

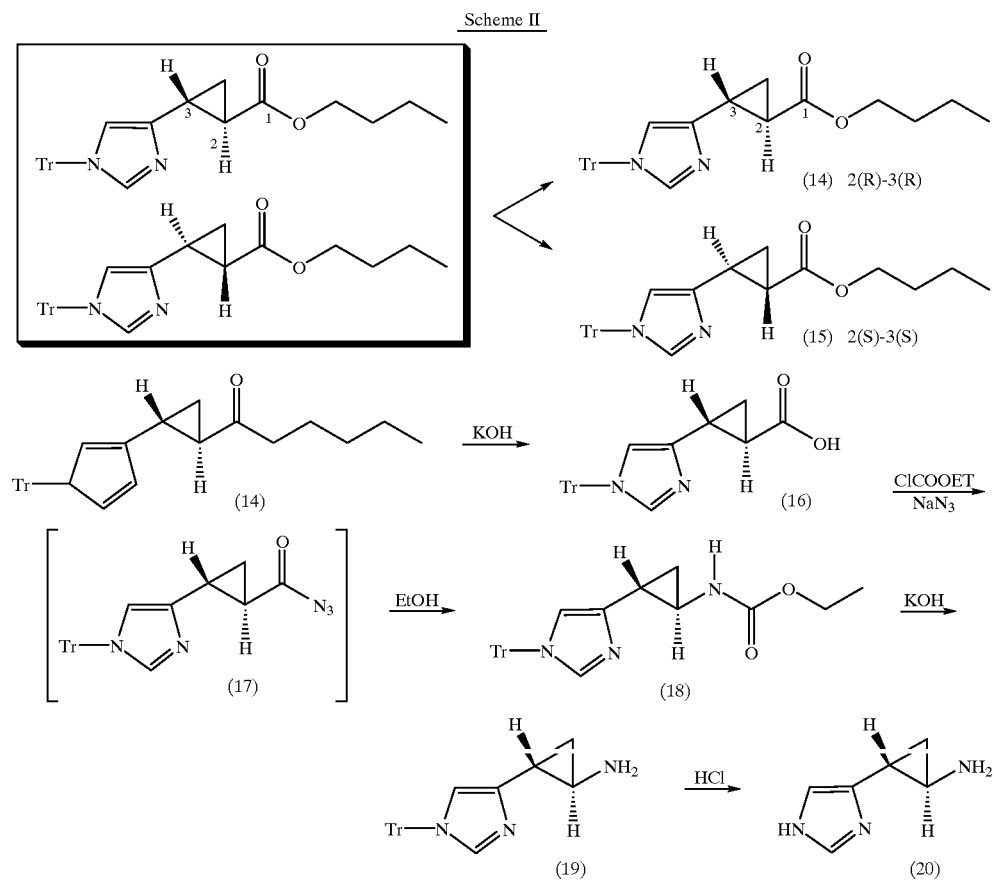

Scheme II

19

Scheme III

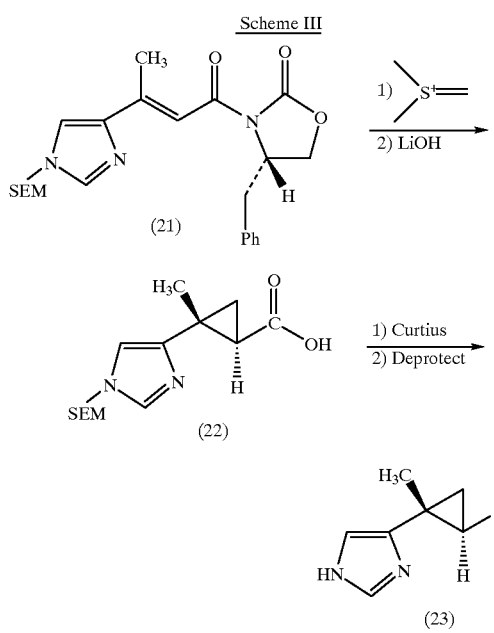

A pathway for the synthesis of trans substituted cyclopropylamine (23) would utilize conjugate addition of sulfur methylides to chiral oxazolidinone (21) followed by LiOH saponification to give acid (22). Curtius rearrangement and deprotection would give cyclopropylamine (23).

Scheme IV

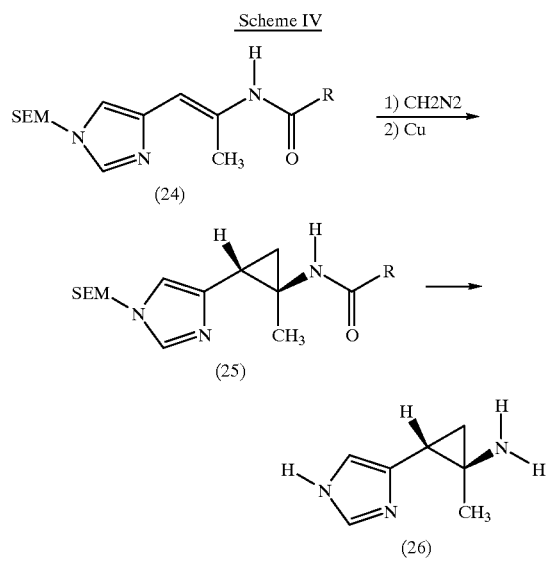

R = chiral auxillary

A pathway for for the synthesis of trans substituted cyclopropylamine (26) would use chiral enamide (24) and a carbene insertion reaction to give (25) followed by hydrolysis to provide (26).

20

C. Preparation of Chiral 5-Membered Ring Amine Compounds

Scheme V

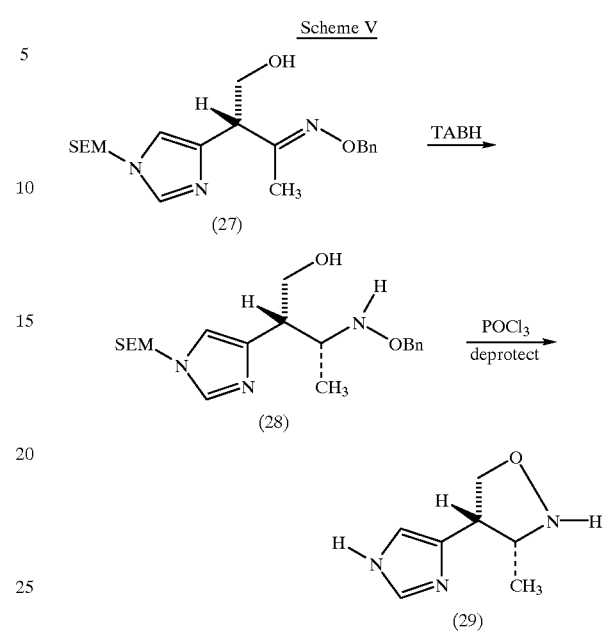

A sequence for the preparation of chiral 5-membered ring amine (29) would make use of tetramethylammonium triacetoxyborohydride (TABH) reduction of hydroxy-oxime (27). Treatment of the N—O— benzyl amine (28) with $POCl_3$ followed by deprotection of the SEM protecting group would give amine (29).

Scheme VI

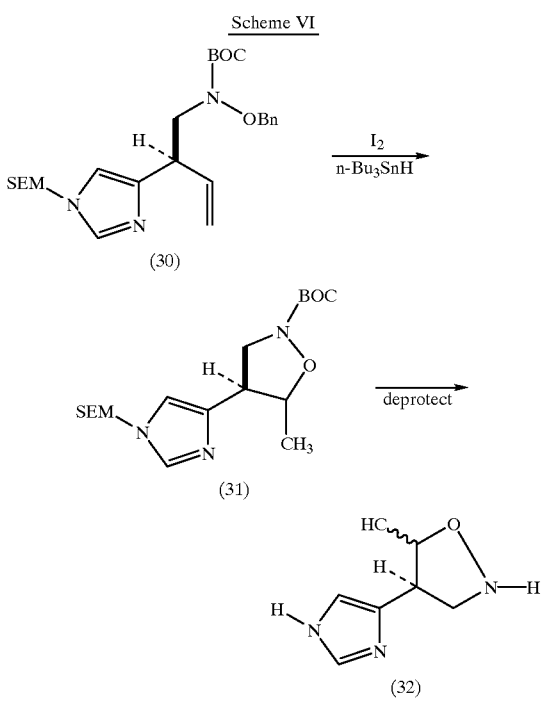

A proposed reaction scheme for the preparation of chiral 5-membered ring amine (30) would make use of Iodide mediated cyclization followed by reduction with $n\text{-}Bu_3SnH$ to give (31). Deprotection of the BOC and SEM protecting groups would afford (32).

EXAMPLE 1

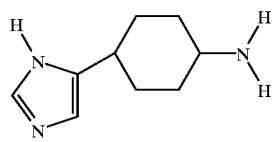

Preparation of 1H-4(5)-imidazoyl-4-cyclohexylamine 1H-4(5)-imidazoyl-4-cyclohexylamine was prepared according to the method outlined by Schunack, *Arch. Pharmaz.* 306, 934–943, (1973) as follows: 4-(4-aminophenyl)-imidazole (3.65 g, 19.2 mM) was dissolved in 50 ml of water and 2.5 ml of HCl. Rh(C) (5%, 2.5 g) was added, and the reaction mixture hydrogenated under 80 atm of $H_2$ for 24 hours in an autoclave. The reaction was filtered through a pad of celite, the pad was washed with water (50 ml) and ethanol (50 ml), and then the filtrate was evaporated in vacuo to give 3.40 grams of 1H-4(5)-imidazoyl-4-cyclohexylamine dihydrochloride.

NMR (300 MHz, $D_2O$): d 8.4 (d, 1H), 7.11 (d, 1H), 3.20 (m, 1H), 2.85 (m, 1H), 1.90 (m, 1H), 1.75 (m, 4H), 1.40 (m, 3H).

Mass Spectrum (DCl, $NH_3$): M+1=166, MW=166.2392, $C_9H_{15}N_3$

EXAMPLE 2

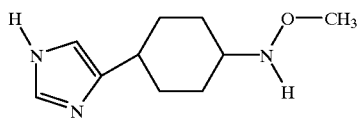

Preparation of 1H-4(5)-imidazoyl-4-cyclohexyl-N-Methoxylamine

Step 1

1-[(2-(trimethylsilyl)ethoxy)]-imidazole (8.0 g, 0.040 m) was dissolved in 100 ml of dry THF and the solution cooled to −78° C. under $N_2$. N-BuLi (17.7 ml, 44.4 m) was added dropwise in ten minutes, and the dark burgundy solution stirred for 1 hour at −78° C. Phenyl disulfide (9.26 g, 42.4 m) in 20 ml of THF was added via syringe, and the reaction mixture stirred for 1 hour. The reaction mixture was added to 500 ml of saturated ammonium chloride solution, and then extracted with 500 ml of ethyl acetate. The ethyl acetate layer was separated, dried over $MgSO_4$, filtered, and evaporated in vacuo to give a yellow oil. Purification using silica gel column chromatography and eluting with ethyl acetate/hexanes mixtures gave 10.0 grams of 1-[2-(trimethylsilyl)ethoxy]methyl]-2-thiophenyl-imidazole (yellow viscous oil).

NMR (300 MHz, $CDCl_3$): d 7.20 (m, 7H), 5.37 (s, 2H), 3.25 (m, 2H), 0.76 (m, 2H), −0.10 (s, 9H)

Step 2

1-[2-(trimethylsilyl)ethoxy]methyl]-2-thiophenyl-imidazole (1.06 g, 3.46 mM) was dissolved in 40 ml of dry THF and the solution cooled to −78° C. under $N_2$. Lithium diisopropylamide (3.46 ml, 5.19 mM, 1.5M solution in cyclohexane from Aldrich) was added via syringe, and the reaction solution stirred for 1 hour at −78° C. N-iodosuccinimide (0.85 g, 3.77 mM) in 10 ml of dry THF was added via syringe, and the reaction stirred for 30 minutes. The reaction mixture was added to 200 ml of saturated ammonium chloride, and extracted with 200 ml of ethyl acetate. The ethyl acetate layer was washed with saturated sodium bisulfite solution (150 ml), separated, dried over $Na_2SO_4$, filtered, and evaporated in vacuo to give a crude red brown oil. Purification by silica gel column chromatography using ethyl acetate/hexanes 1:9 gave 1.089 grams of 1-[2-(trimethylsilyl)ethoxy]methyl]-2-thiophenyl-5-iodo-imidazole (orange viscous oil).

NMR (300 MHz, $CDCl_3$): d 7.28 (s, 1H), 7.23 (m, 5H), 5.40 (s, 2H), 3.44 (m, 2H), 0.80 (m, 2H), −0.06 (s, 9H).

Step 3

To a dichloromethane (500 ml) solution of mcpba (4.15 g, 14.46 mM, 60% purity from Aldrich) cooled to 50° C. was added a dichloromethane solution (50 ml) of 1-[2-(trimethylsilyl)ethoxy]methyl]-2-thiophenyl-5-iodo-imidazole (3.0 g, 7.23 mM). The reaction mixture was stirred for 24 hours, warming to r.t. The reaction mixture was added to 500 ml of 10% sodium bisulfite solution, separated, washed with 10% sodium bicarbonate solution (500 ml), separated, dried over $Na_2SO_4$, filtered, and evaporated in vacuo to give a crude yellow solid. Purification by silica gel column chromatography using ethyl acetate/hexanes 1:9 then 2:8 gave 1.65 grams of of 1-[2-(trimethylsilyl)ethoxy]methyl]-2-sulphonylphenyl-5-iodo-imidazole (white solid).

NMR (300 MHz, $CDCl_3$): d 8.04 (m, 2H), 7.58 (m, 3H), 7.23 (s, 1H), 5.66 (s, 2H), 3.44 (m, 2H), 0.82 (m, 2H), −0.03 (s, 9H).

Mass Spectrum (FAB): M+1=465.3, MW=464.3963

Step 4

1-[2-(trimethylsilyl)ethoxy]methyl]-2-sulphonylphenyl-5-iodo-imidazole (0.430 g, 0.96 mM) was dissolved in 16 ml of dry dichloromethane and the reaction solution cooled to 0° C. under $N_2$. t-Butylmagnesium chloride (1.00 ml, 1.0 mM, 1.0 M solution in THF from Aldrich) was added dropwise in 5 minutes, and the reaction solution left to stir for 1 hour at 0–5° C. 1,4-cyclohexanedione mono-ethylene ketal (0.150 g, 0.96 mM) in 5 ml of dry dichloromethane was added via syringe, the reaction mixture stirred for an additional 30 minutes at 5° C., then warmed to r.t. over 1.5 hours. The reaction was quenched by adding 50 ml of saturated ammonium chloride, and then extracted with chloroform (2×50 ml), separated, dried over $MgSO_4$, filtered, and evaporated in vacuo to give a crude yellow oil. Purification using silica gel column chromatography and eluting with ethyl acetate/hexanes 2:8, then 1:1 gave 340 mgs of 1-(1-[2-(trimethylsilyl)ethoxy]methyl]-2-sulphonylphenyl-5-imidazoyl)-cyclohexanol-4-mono ethylene ketal (white foam).

NMR (300 MHz, $CDCl_3$): d 8.01 (m, 2H), 7.55 (m, 3H), 7.00 (s, 1H), 5.6 (s, 2H), 3.93 (m, 4H), 3.41 (m, 2H), 2.55 (s, 1H,—OH), 1.96 (m, 6H), 1.58 (m, 2H). 0.78 (m, 2H), −0.02 (s, 9H).

Mass Spectrum (DCl, $NH_3$): M+1=495, MW=494.6839, $C_{23}H_{34}N_2O_6S_1Si_1$

Step 5

1-(1-[2-(trimethylsilyl)ethoxy]methyl]-2-sulphonylphenyl-5-imidazoyl)-cyclohexanol-4-mono ethylene ketal (0.10 g, 0.20 mM) was dissolved in 8 ml of dry methanol at r.t. under $N_2$. $NaH_2PO_4$ (0.085 g, 0.70 mM) was added, and then 2% Na (Hg) (2.0 g) was added in portions. The reaction mixture was stirred for 3 hours, and then filtered through a pad of celite. The methanol filtrate was evaporated and the residue partioned between CHCl₃ (50 ml) and saturated ammonium chloride solution (50 ml). The chloroform layer was separated, dried over MgSO₄, filtered, and evaporated in vacuo to give a white foam. Purification using thin layer chromatography and eluting with ethyl acetate gave 65 mgs of 1-(1-[2-(trimethylsilyl) ethoxy] methyl]-5-imidazoyl)-cyclohexanol-4-mono ethylene ketal.

NMR (300 MHz, CDCl₃): d 7.50 (s, 1H), 6.86 (s, 1H), 5.20 (s, 2H), 3.94 (m, 4H), 3.45 (m, 2H), 2.55 (br s, 1 H,–OH), 2.02 (m, 6H), 1.64 (m, 2H), 0.87 (m, 2H), 0.0 (s, 9H).

Mass Spectrum (DCl, NH₃): M+1=355, MW=354.5259, $C_{17}H_{30}N_2O_4Si_1$

Step 6

1-(1-[2-(trimethylsilyl)ethoxy]methyl]-5-imidazoyl)-cyclohexanol-4-mono ethylene ketal (0.190 g, 0.53 mM) and PPTS (30 mgs) were heated at reflux in 10 ml of THF and 2 drops of water for 4 hours. The reaction mixture was cooled, added to 20 ml of saturated ammonium chloride, and extracted with ethyl acetate (50 ml). The ethyl acetate layer was separated, dried over MgSO₄, filtered, and evaporated in vacuo to give a yellow oil. Purification using thin layer chromatography and eluting with ethyl acetate/hexanes 1:1 gave 90 mgs of 1-(1-[2-(trimethylsilyl)ethoxy]methyl]-5-imidazoyl)-cyclohexen-4-mono ethylene ketal (yellow oil).

NMR (300 MHz, CDCl₃): d 7.48 (d, 1H), 6.9 (d, 1H), 6.35 (m, 1H), 5.2( s, 2H), 4.00 (s, 4H), 3.42(m; 2H), 2.56 (m, 2H), 2.43 (m, 2H), 1.88 (m, 2H), 0.87 (m, 2H), 0.0 (s, 9H).

Step 7

1-(1-[2-(trimethylsilyl)ethoxy]methyl]-5-imidazoyl)-cyclohexen-4-mono ethylene ketal (0.085 g, 0.25 mM) was dissolved in 8 ml of dry THF. n-Butyl ammonium fluoride (0.275 ml, 1.0M solution in THF from Aldrich) was added, and the reaction heated at 60° C. for 6 hours. The reaction was cooled, added to 50 ml of saturated ammonium chloride solution, and extracted with chloroform (2×50 ml). The chloroform layer was separated, dried over MgSO₄, filtered, and evaporated in vacuo to give crude yellow oil. Purification using silica gel column chromatography and eluting with ethyl acetate/hexanes/NH₃ 40/60/0.1% gave 60 mgs of 1-[1H-5-imidazoyl)-cyclohexen-4-mono ethylene ketal (yellow oil).

NMR (300 MHz, CDCl₃): d 7.48 (d, 1H), 6.9 (d, 1H), 6.35 (m, 1H), 4.00 (s, 4H), 2.56 (m, 2H), 2.43 (m, 2H), 1.88 (m, 2H).

Mass Spectrum (DCl,NH₃): M+1=207, MW=206.2464, $C_{11}H_{14}N_2O_2$

Step 8

1-[1H-5-imidazoyl)-cyclohexen-4-mono ethylene ketal (1.00 g, 4.84 mM) was dissolved in 75 ml of methanol. 0.1 gram of 10% Pd(C) was added and stirred for 16 hours under 20 atm of hydrogen pressure in an autoclave. The reaction mixture was filtrated over a short celite column, concentrated in vacuo and washed with methanol to give 0.90 grams of 1-[1H-5-imidazoyl)-cyclohexane-4-mono ethylene ketal (colorless viscous oil).

NMR (300 MHz, CDCl₃): d 7.48 (d, 1H), 6.9 (d, 1H), 4.00 (s, 4H), 2.56 (m, 2H), 2.43 (m, 2H), 2.24 (m, 1H), 1.18 (m, 4H).

Mass Spectrum (DCl,NH₃): M+1=209, MW=208.2624, $C_{11}H_{16}N_2O_2$

Step 9

1-[1H-5-imidazoyl)-cyclohexane-4-mono ethylene ketal (0.600 g, 2.88 mM) was dissolved in 10 ml of THF. 8 ml of 5% HCl was added and the reaction stirred at r.t. for 20 hrs. 100 ml of ethyl acetate and 50 ml of 10% NaOH solution was added to the reaction mixture, the ethyl acetate layer separated, dried over MgSO₄, filtered, and evaporated in vacuo to give a crude yellow oil. Purification using silica gel column chromatography and eluting with ethyl acetate/ hexanes/0.1% NH₃ gave 500 mgs of 4-[1H-5-imidazoyl)-cyclohexanone.

NMR (300 MHz, CDCl₃): d 7.48 (d, 1H), 6.9 (d, 1H), 2.56 (m, 2H), 2.43 (m, 2H), 2.24 (m, 1H), 1.18 (m, 4H).

Mass Spectrum (DCl,NH₃): M+1=151, MW=150.2017, $C_9H_{12}N_1O_1$

Step 10

4-[1H-5-imidazoyl)-cyclohexanone (0.500 g, 3.31 mM) was dissolved in 20 ml of methanol and 20 ml of THF at r.t. Triethylamine (1.05 ml,7.5 mM) was added, followed by the addition of methoxylamine hydrochloride (0.414 g,4.96 mM). The reaction solution was stirred at 50° C. for 20 hours. Ethyl acetate (100 ml) and 150 ml of saturated ammonium chloride solution were added, the ethyl acetate layer separated, dried over MgSO₄, filtered, and evaporated in vacuo to give 450 mgs of crude 4-[1H-5-imidazoyl)-cyclohexanone-N-methoxy oxime. The crude oximes obtained were directly reduced by addition of tetramethylimmonium triacetoxyimmoniumborohydride (TABH). (3.35 mM) to a THF (50 ml) solution of crude oximes at 0° C. under N₂. The reaction was quenched by the slow addition of water, the reaction mixture was extracted with chloroform (3×50 ml), the chloroform layer separated, dried, filtered, and evaporated in vacuo to give a yellow oil. Purification using silica gel column chromatography and eluting with CHCl₃/Methanol/0.1% NH₃ gave 350 mgs of 4-[1H-5-imidazoyl)-cyclohexyl-N-methoxy amine.

NMR (300 MHz, CDCl₃): d 7.48 (d, 1H), 6.9 (d, 1H), 3.50 (s, 3H), 2.30 (m, 1H), 2.16 (m, 2H), 2.13 (m, 2H), 2.24 (m, 1H), 1.18 (m, 4H).

Mass Spectrum (DCl,NH₃): M+1=196, MW=195.266, $C_{10}H_{17}N_3O_1$

EXAMPLE 3

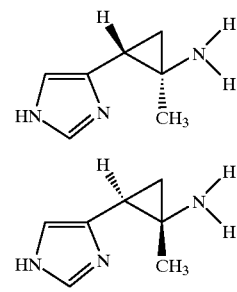

Preparation of Racemic 2(R)-(1H-4-imidazoyl)-3(R)-methyl cyclopropyl amine and 2(S)-(1H-4-imidazoyl)-3(S)-methyl-cyclopropyl amine Step 1

To 2.4 mmoles of $Me_2SO^+ I^-$ and 2.4 mmoles of NaH (60% in mineral oil) under N₂ was added dropwise with stirring 10 cc of dry DMSO. After all the DMSO had been added, the mixture was stirred for 30 minutes, and then a solution of 3-[1-Triphenylmethyl-5-imidazoyl]-2-methyl-2-propenyl-butyl ester (1.0 gram, 2.22 mmoles) in 20 cc of dry DMSO and THF (1:1) was added dropwise. The reaction was heated at 60° C. for 24 hours, cooled, and poured into cold 25 cc of 1M Hcl. The mixture was extracted with ether (2×100 cc), the ether extract separated, dried over $MgSO_4$, filtered, and evaporated in vacuo. The residue was purified by solica gel column chromatography using ethyl acetate/hexanes (4:6) to give 0.85 grams of 3-[1-Triphenylmethyl-5-imidazoyl]-2-methyl-2-cyclopropyl-butyl ester.

Step 2

A solution of 3-[1-Triphenylmethyl-5-imidazoyl]-2-methyl-2-cyclopropyl-butyl ester (1.4 g, 30 mmoles) in ETOH (15 cc) was stirred at 40–50° C. while 15 cc of 12% aqueous KOH was added in portions. After stirring at 60° C. for 24 hours, the solution was cooled, diluted with water (30 cc), extracted with with ether and then acidified to pH=6.0 with 0.5M Hcl. The precipitate obtained was filtered off and dried to give 1.2 grams of 3-[1-Triphenylmethyl-5-imidazoyl]-2-methyl-2-cyclopropylcarboxylic acid.

Step 3

3-[1-Triphenylmethyl-5-imidazoyl]-2-methyl-2-cyclopropylcarboxylic acid (1.0 grams, 2.5 mmoles) was dissolved in 50 cc of dry THF and cooled to 0° C. under $N_2$ Triethylamine (2.5 mmoles) was added followed by dropwise addition of ethyl chloroformate (2.5 mmoles). The reaction mixture was stirred at 0° C. for 30 minutes, and then sodium azide (2.5 mmoles) in 30 cc of water was added. After stirring for 1 hour, the crude acyl azide was extracted with ether (100 ml), the ether layer separated, then treated with ethanol, heated to remove the ether, and then refluxed for 12 hours. The reaction mixture was cooled, and the organic volatiles evaporated in vacuo. The crude carbamate obtained was subjected to saponification with KOH (2 grams) in 30 cc of ethanol under $N_2$ for 12 hours under reflux. The mixture was cooled, 100 cc of water added, and extracted with ethyl acetate (100 ml). The ethyl acetate layer was separated, dried over $MgSO_4$, filtered, and evaporated in vacuo. Purification by silica gel column chromatography using ethyl acetate/hexanes (1:1) gave 0.600 grams of a yellow oil, 2-[1-Triphenylmethyl-5-imidazoyl]-1-methylcyclopropylamine.

NMR ($CDCl_3$, 300 Mhz): 7.3 (m, 9H), 7.1 (m, 6H), 6.5 (s, 1H), 2.60 (m, 1H), 1.65 (s, 3H) 1.2 (m, 1H), 0.95 (m, 1H).

Mass Spectrum (DCl, $NH_3$): 365 $(M+1)^+$, MW=365.4994, $C_{26} H_{25} N_2$

Step 4

2-[1-Triphenylmethyl-5-imidazoyl]-1-methylcyclopropylamine (0.600g) was dissolved in 5 cc of ethanol and added to 50 cc of 2N Hcl. The mixture was refluxed for 1 hour, cooled, filtered, and the filtrate evaporated in vacuo. The tan solid remaining was triturated with ether, and collected by filtration, washing with ether, to give 200 mgs of racemic 2(R)-(1H-4-imidazoyl)-3(R)-methylcyclopropylamine dihydrochloride salt and 2(S)-(1H-4-imidazoyl]-3(S)-methylcyclopropylamine dihydrochloride salt.

NMR ($D_2O$, 300 Mhz): 8.46 (s, 1H), 7.14 (s, 1H), 2.9 (m, 1H) 1.8 (s, 3H), 1.42 (m, 1H), 1.16 (m, 1H).

The compounds of this invention are agonists of the histamine $H_3$ receptor. The binding affinity of the compounds of the invention to the $H_3$ receptor may be demonstrated by the procedure described below:

In Vitro Histamine $H_3$ Receptor Binding Analysis

Histamine $H_3$ receptor affinity was determined in rat cortical membranes using the $H_3$ selective agonist ligand, [$^3$H]-$N^\alpha$-methylhistamine (78.9 Ci/mmole, DuPont NEN Research Products, Boston, Mass.) according to the method of West et al., (1990) Mol. Pharmacol. 38: 610–613 with modifications. Briefly, animals were sacrificed by decapitation and the cerebral cortex was rapidly removed. Rat cortices were mechanically homogenized with an Omni 1000 motor driven homogenizer in 10 volumes (wt/vol) of Krebs-Ringers Hepes buffer (pH 7.4) containing the following protease inhibitors; EDTA (10 mM), PMSF (0.1 mM), chymostatin (0.2 mg/50 mL) and leupeptin (0.2 mg/50 mL). The homogenate was centrifuged in a Sorvall at ~40,000× g for 30 min. The pellet was resuspended by mechanical homogenization in 25 mL water and lysed on ice for 30 min. The homogenate was recentrifuged and the membrane lysis was repeated. The membranes were recentrifuged and the final pellet was resuspended in 14 volumes of water to give approximately 200 µg protein/100 µl final concentration. The suspension was stored at −80° C. prior to use. Protein concentrations were determined by Coomassie Plus Protein Assay (Pierce, Rockford, Ill.).

The binding assay was carried out in polypropylene tubes in a total volume of 0.4 ml of 50 mM $Na^+$ Phosphate buffer (pH 7.4), containing 150–200 µg of tissue protein, 0.8–1.2 nM [$^3$H]-$N^\alpha$-methylhistamine and 0.3 to 10,000 nM GT-2016. Nonspecific binding (NSB) was accounted for by the inclusion of thioperamide (10 µM). Samples were incubated for 40 minutes at 25° C. The samples were filtered through glass fiber strips, pre-washed with 0.3% polyethyleneimine, using a Brandell cell harvester. The filters were rapidly washed three times with 4 ml of 25 mm Tris buffer containing 145 mM NaCl (pH 7.4, 4° C.). Filters were transferred to polyethylene minivials and counted in 3.5 ml of scintillation fluid (Ecolume, ICN Biomedicals, Inc.). Using this procedure, the non-specific binding was less than 10% of the total binding and the binding to the glass fiber filters was negligible. Saturation and competition experiments were analyzed with the ReceptorFit saturation and competition curve fittingprograms (Lundon Software, Inc., Cleveland, OH). K's were determined using the equation $K_i = IC_{50}/(1+([Ligand]/[K_d]))$. The results are given in Table 1.

TABLE 1

| Histamine $H_3$ Receptor Binding Affinities | | |
|---|---|---|
| Example # | Structure | $H_3$ Receptor $K_i$ (nM) |
| 1 | 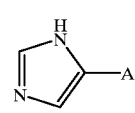 | 20.0 |

What is claimed is:
1. A compound of formula

I wherein A is
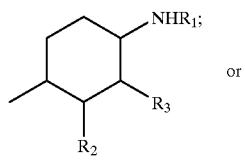
or
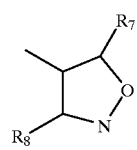
where
R$_1$ is lower alkyl or lower alkoxy;
R$_2$, R$_3$, R$_7$ and R$_8$ are each independently hydrogen or lower alkyl.
2. A compound or a pharmaceutically acceptable salt or solvate thereof as in claim 1 selected from the group consisting of:
(1.0)
(2.0)
(3.0)
(4.0)
(5.0)
(6.0)
(7.0)
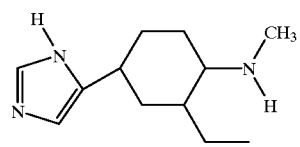
(8.0)
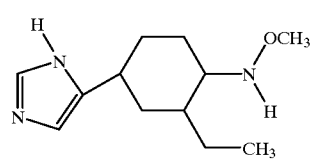
(9.0)
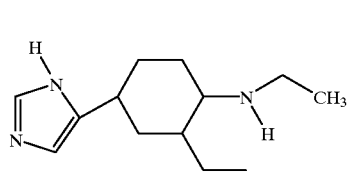
(10.0)
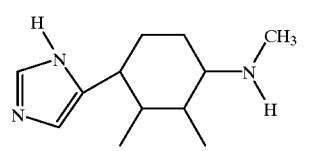
(11.0)
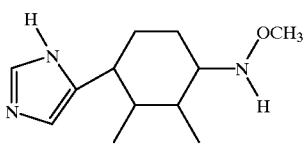
(12.0)
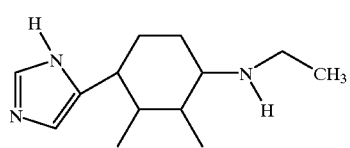
(13.0)
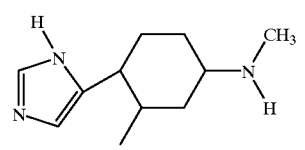
(14.0)
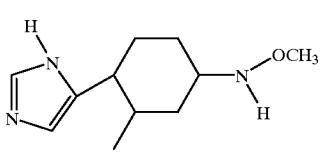
(15.0)
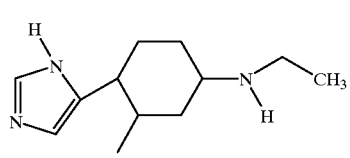

-continued (32.0) 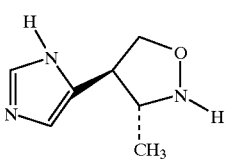

(33.0) 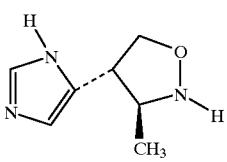

(34.0) 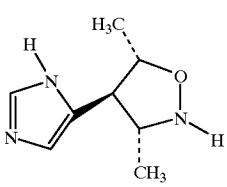

(35.0) 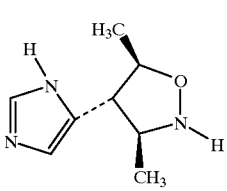

(36.0) 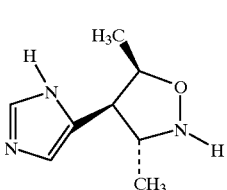

(37.0) 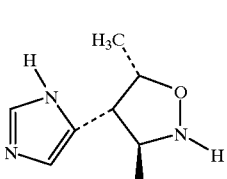

(38.0) 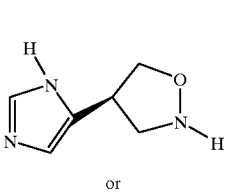

or (39.0) 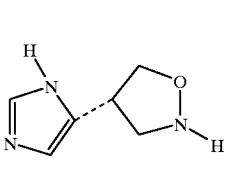

3. A compound of formula:

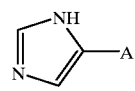

wherein A is

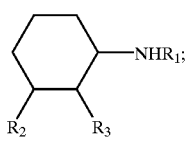

where
- $R_1$ is lower alkyl or lower alkoxy;
- $R_2$ and $R_3$ are each independently hydrogen or lower alkyl.

4. A compound of formula:

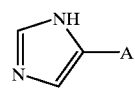

wherein A is

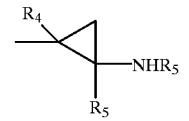

where
- $R_4$ and $R_5$ are each independently hydrogen or lower alkyl;
- $R_6$ is hydrogen, lower alkyl or lower alkoxy and $R_5$ and $R_6$ when joined form a 4, 5, or 6 membered ring, with the proviso that when $R_4$ and $R^5$ are both hydrogen, $R_6$ is not hydrogen.

5. A compound of formula:

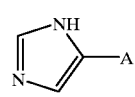

wherein A is

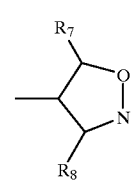

where $R_7$ and $R_8$ are each independently hydrogen or lower alkyl.

6. A pharmaceutical composition comprising at least one compound of claim 1 and a pharmaceutically acceptable carrier.

7. A method of preparing a pharmaceutical composition comprising admixing a compound of claim 1 with a pharmaceutically acceptable carrier.

8. A method of treating conditions of allergy, inflammation, cardio or cerebrovascular disease, gastrointestinal disorders psychiatric disorders, sleep disorders or hypothalamic dysfunction comprising administering to a patient in need of such treatment, an effective amount of a compound of claim 1.

9. A method of activating histamine H₃ receptors comprising administering to a patient in need of such activation an effective amount of at least one compound of claim 1.

10. A compound selected from the group consisting of: 2(R)-(1H-4-imidazoyl)-3(R)-cyclopropylamine and 2(S)-(1H-4-imidazolyl)-3(S)-cyclopropylamine.

11. A method of treating conditions of allergy, inflammation, cardio or cerebrovascular disease, gastrointestinal disorders, psychiatric disorders, sleep disorders and hypothalamic dysfunction, comprising administering to a patient in need of such treatment, an effective amount of a compound selected from the group consisting of: 2(R)-(1H-4-imidazoyl)-3(R)-cyclopropylamine and 2(S-(1H-4-imidazoyl)-3(S)-cyclopropylamine.

12. A method of activating histamine H₃ receptors comprising administering to a patient in need of such activation an effective amount of at least one compound selected from the group consisting of: 2(R)-(1H-4imidazoyl)-3(R)-cyclopropylamine and 2(S)-(1H-4-imidazoyl)-3(S)-cyclopropylamine.

13. A compound or a pharmaceutically acceptable salt or solvate thereof as in claim 4 selected from the group consisting of:

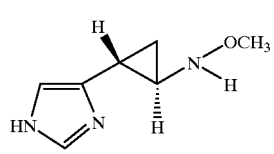
(16.0)

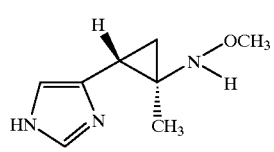
(17.0)

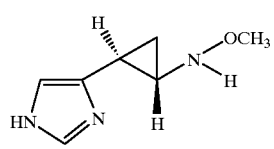
(18.0)

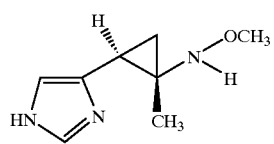
(19.0)

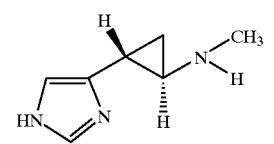
(20.0)

-continued

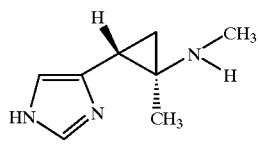
(21.0)

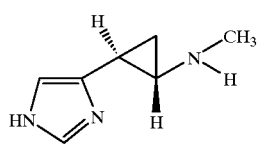
(22.0)

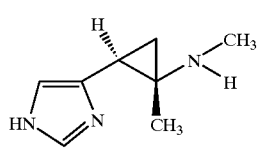
(23.0)

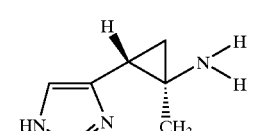
(24.0)

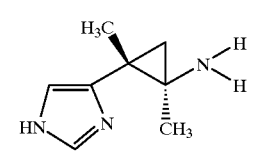
(25.0)

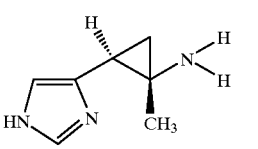
(26.0)

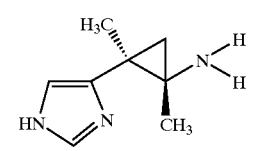
(27.0)

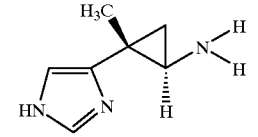
(28.0)

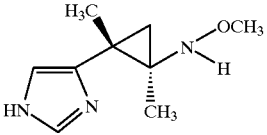
(29.0)

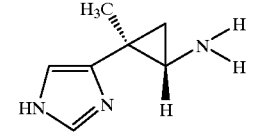
(30.0)

-continued

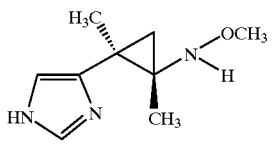

(31.0)

14. A pharmaceutical composition comprising at least one compound of claim 4 and a pharmaceutically acceptable carrier.

15. A method of preparing a pharmaceutical composition comprising admixing a compound of claim 4 with a pharmaceutically acceptable carrier.

16. A method of treating conditions of allergy, inflammation, cardio or cerbrovascular disease, gastrointestinal disorders, psychiatric disorders, sleep disorders and hypothalmic dysfunction, comprising administering to a patient in need of such treatment, an effective amount of a compound of claim 4.

17. A method of activating histamine $H_3$ receptors comprising administering to a patient in need of such activation an effective amount of at least one compound of claim 4.

* * * * *

UNITED STATES PATENT AND TRADEMARK OFFICE
CERTIFICATE OF CORRECTION

PATENT NO. : 6,072,057
DATED : June 6, 2000
INVENTOR(S) : J.G. Phillips et al.

It is certified that error appears in the above-identified patent and that said Letters Patent is hereby corrected as shown below:

Title page,
ABSTRACT,
Please delete "effective amount of a compound of formula (1)" and insert -- effective amount of a compound of formula (I) --.

Column 2,
Line 17, please delete "ad" and insert -- and --.
Lines 26 and 28, delete "a $H_3$" and insert -- an $H_3$ --.
Line 40, please delete "to be to regulated" and insert -- to be regulated --.

Column 4,
Line 63, please delete "them" and insert -- the --.

Column 12,
Line 27, please delete "othermineral" and insert -- other minerals --.
Line 54, please delete "properties,".
Line 65, please delete "n-propxy, iso-propxy" and insert -- n-propoxy, iso-propoxy --.

Column 13,
Line 43, please delete "emulsifying in" and insert -- or emulsifying agents. In --.

Column 14,
Line 8, please delete "carboxymethylccilulose" and insert -- carboxymethylcellulose --.
Line 16, please delete "such calcium" and insert -- such as calcium --.

Column 15,
Line 26, please delete "comtemplated" and insert -- contemplated --.
Line 31, please delete "compounds of formula" and insert -- compounds of --.

Column 18, Scheme II,
Please delete "ClCOOET" and insert -- ClCOOEt --.

UNITED STATES PATENT AND TRADEMARK OFFICE
CERTIFICATE OF CORRECTION

PATENT NO. : 6,072,057
DATED : June 6, 2000
INVENTOR(S) : J.G. Phillips et al.

It is certified that error appears in the above-identified patent and that said Letters Patent is hereby corrected as shown below:

Column 17, Scheme II,
Please delete the structure for compound 14 and replace it with

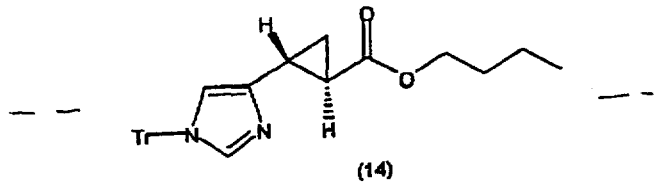

Column 18,
Line 4, please delete "receptor receptor agonists" and insert -- receptor agonists --.
Line 7, please delete "-2(1S, 2S)-" and insert -- -2(S)-3(S)- --.
Line 24, please delete "2-(R)(1H)" and insert -- 2(R)-(1H --.
Line 25, please delete "cyclopropylamine-cyclopropylamine" and insert
-- cyclopropylamine --.

Column 19,
Line 64, please delete "for for the" and insert -- for the --.

Column 21,
Line 22, please delete "d 8.4" and insert -- δ 8.4 --.
Line 42, please delete "N-BuLi" and insert -- n-BuLi --.
Line 55, please delete "d 7.20" and insert -- δ 7.20 --.
Line 65, please delete N-iodosuccinimide" and insert -- N-Iodosuccinimide --.

Column 22,
Line 9, please delete "d 7.28" and insert -- δ 7.28 --.
Line 14, please delete "mcpba" and insert -- MCPBA --.
Line 24, please delete "1.65 grams of of" and insert -- 1.65 grams of --.
Line 26, please delete "d 8.04" and insert δ 8.04 --.
Line 52, please delete d 8.01" and insert -- δ 8.01 --.

UNITED STATES PATENT AND TRADEMARK OFFICE
CERTIFICATE OF CORRECTION

PATENT NO. : 6,072,057
DATED : June 6, 2000
INVENTOR(S) : J.G. Phillips et al.

It is certified that error appears in the above-identified patent and that said Letters Patent is hereby corrected as shown below:

Column 23,
Line 8, please delete "d 7.50" and insert -- δ 7.50 --.
Lines 26, 44 and 59, please delete "d 7.48" and insert -- δ 7.48 --.

Column 24,
Lines 9 and 36, please delete "d 7.48" and insert -- δ 7.48 --.

Column 25,
Lines 3, 16 and 50, please delete "Hcl" and insert -- HCl --.
Line 12, please delete "ETOH" and insert -- EtOH --.
Lines 39 and 49, please delete "0.600" and insert -- 0.60 --.
Line 42, please delete "Mhz): 7.3" and insert -- MHz): δ 7.3 --.
Line 58, please delete "Mhz): 8.46" and insert -- MHz): δ 7.46 --.

Column 26,
Line 41, please delete "fittingprograms" and insert -- fitting programs --.

Column 30, claim 4,
Please delete

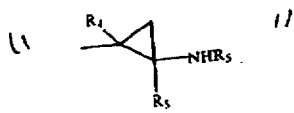

and insert

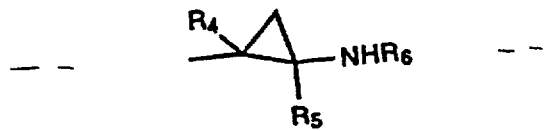

UNITED STATES PATENT AND TRADEMARK OFFICE
CERTIFICATE OF CORRECTION

PATENT NO. : 6,072,057
DATED : June 6, 2000
INVENTOR(S) : J.G. Phillips et al.

It is certified that error appears in the above-identified patent and that said Letters Patent is hereby corrected as shown below:

Column 31, claim 8,
Line 4, please delete "or hypothalamic" and insert -- and hypothalamic --.

Column 31, claim 11,
Line 7, please delete "2(S-(1H" and insert -- 2(*S*)-(1H --.

Column 34, claim 16,
Line 2, please delete "cerbrovascular" and insert -- cerebrovascular --.
Line 4, please delete "hypothalmic" and insert -- hypothalamic --.

Signed and Sealed this

Fifth Day of February, 2002

Attest:

JAMES E. ROGAN
*Attesting Officer*  *Director of the United States Patent and Trademark Office*